US010215897B1

(12) United States Patent
Cahill et al.

(10) Patent No.: US 10,215,897 B1
(45) Date of Patent: Feb. 26, 2019

(54) INFRARED LIGHT ABSORBING AMINIUM AND DIIMMONIUM COMPOSITIONS

(71) Applicant: Noticxe, Inc., Dayton, OH (US)

(72) Inventors: Paul A. Cahill, Dayton, OH (US); Richard Steppel, Dayton, OH (US)

(73) Assignee: NOTICXE, INC., Dayton, OH (US)

( * ) Notice: Subject to any disclaimer, the term of this patent is extended or adjusted under 35 U.S.C. 154(b) by 172 days.

(21) Appl. No.: 15/013,331

(22) Filed: Feb. 2, 2016

(51) Int. Cl.
| | |
|---|---|
| *G03C 1/00* | (2006.01) |
| *G02B 5/20* | (2006.01) |
| *G02B 1/04* | (2006.01) |
| *G02C 7/10* | (2006.01) |
| *C08G 64/42* | (2006.01) |
| *C07F 5/02* | (2006.01) |
| *C07C 211/64* | (2006.01) |

(52) U.S. Cl.
CPC ............ *G02B 5/208* (2013.01); *C07C 211/64* (2013.01); *C07F 5/027* (2013.01); *C08G 64/42* (2013.01); *G02B 1/043* (2013.01); *G02C 7/108* (2013.01)

(58) Field of Classification Search
USPC .............................................. 430/108.9, 339
See application file for complete search history.

(56) References Cited

U.S. PATENT DOCUMENTS

| | | | |
|---|---|---|---|
| 3,341,464 | A | 9/1967 | Susi et al. |
| 3,400,156 | A | 9/1968 | Milionis et al. |
| 3,440,257 | A | 4/1969 | Susi et al. |
| 3,484,467 | A | 12/1969 | Susi et al. |
| 3,575,871 | A | 4/1971 | Susi et al. |
| 3,631,147 | A | 12/1971 | Susi et al. |
| 7,498,123 | B2 * | 3/2009 | Cahill .................. B41M 5/465 430/108.2 |

FOREIGN PATENT DOCUMENTS

GB      1103850 A      2/1968

OTHER PUBLICATIONS

Gorvin, John H., "The Synthesis of Di- and Tri-arylamines Through Halogen Displacement by Base-Activated Arylamines: Comparison with the Ullmann Condensation," J. Chem. Soc. Perkin Trans. I, pp. 1331-1335 (1988).

Nieunhoeffer, Otto et al., "Das Tris-[p-dimethylamino-phenyl]-ammeniumkation, ein durch Mesomerie stabilisiertes, bestandiges, freies Stickstoffradikal," and English-language Abstract, Aus Dem II. Chemischen Institut der Humboldt-Universitat, Berlin, pp. 245-251 (Sep. 1958).

* cited by examiner

*Primary Examiner* — Monique R Peets
(74) *Attorney, Agent, or Firm* — Dinsmore & Shohl LLP

(57) ABSTRACT

Disclosed are infrared light absorbing aminium and diimmonium compositions that have at least one absorption maximum in the infrared spectral region between about 700 and 1500 nm and that are useful, for example, as infrared absorbers. In one example, an infrared light aminium absorbing composition includes an anionic borate moiety and an aminium radical cation, which has at least one absorption peak in the near infrared wavelength region between about 700 and 1500 nm. In another example, an infrared light diimmonium absorbing composition includes two anionic borate moieties and a diimmonium radical cation, which has at least one absorption peak in the near infrared wavelength region between about 700 and 1500 nm. Such compositions may be incorporated into films or bulk materials to form light filters for electromagnetic radiation, including laser radiation.

22 Claims, 3 Drawing Sheets

INFRARED LIGHT ABSORBING AMINIUM AND DIIMMONIUM COMPOSITIONS

GOVERNMENT CONTRACT SUPPORT CLAUSE

This invention was made with Government support under Contract Number FA8650-09-D-5430, awarded by the U.S. Air Force; the United States Federal Government, therefore, has certain rights in the invention.

FIELD OF THE INVENTION

The present invention relates to infrared light absorbing compositions for manipulating light, and more specifically, to long-wavelength infrared light absorbing aminium or diimmonium compositions that have at least one absorption maximum between about 700 nm and 1500 nm, and filters or sensing materials including such compositions.

BACKGROUND OF THE INVENTION

There are many applications in which dyes, including infrared light absorbing compositions, when dissolved or dispersed in a host liquid, solid or gel, provide light absorption and, in some cases, fluorescent or phosphorescent light emission. For example, non-luminescent or weakly luminescent infrared compositions are used in light filters. Luminescence encompasses all light emission whether by fluorescence, phosphorescence, or an undetermined emission mechanism. Such infrared light filters are utilized in sensors, including solid state detectors, photodiode arrays, imaging (camera) sensors (charge-coupled devices (CCD) and complementary metal oxide semiconductor (CMOS)), and other devices, to shape the sensitivity curve of a broadly photosensitive element(s), for example, by absorbing invisible light to provide a responsivity curve similar to that of the eye. Filters including such infrared absorbing compositions are also used to protect sensors or the eye from infrared radiation, for example, laser radiation or other sources of infrared light, such as welding operations or arc flash. Infrared wavelength filters may also be used to diminish the intensity of the infrared light energy emitted from natural or artificial illumination sources, from information displays, including CRTs, liquid crystal and plasma displays, light emitting diodes, and other emissive technologies such as organic light-emitting diodes (OLEDs), especially in cases where such infrared light sources may interfere with the operation of infrared sensors. Infrared absorbing compositions may also be used to provide infrared blocking in otherwise infrared transparent or partially infrared transparent plastic articles, e.g., banking or credit cards, in which visibly partially transparent plastics provide for marketing or security features. Infrared absorbing compositions may also be used in cell biology applications, in inks or in heat activated compositions.

Infrared absorbing compositions have a long history and thousands are known. Infrared absorbing compositions may also be categorized into several other classes of chemical compounds including, among others, polymethine dyes, the phthalocyanines and their metal complexes, naphthalocyanines and their metal complexes, anthraquinone derivatives, rylenes, dithiolenes (also known as metal complex dyes), aminium salts, and diimmonium salts. Polymethines and unsubstituted phthalocyanines and naphthalocyanines have relatively narrower absorption bands than dithiolenes, anthraquinone derivatives, aminium salts or diimmonium salts. Both narrow and broad band absorbing compositions are useful because each has performance advantages in certain applications.

The first report of the spectral properties of infrared light absorbing aminium dyes was by Neunhoeffer et al., Chemische Berichte 92, 245-251 (1959). Subsequent development of these dyes at American Cyanamide by Milionis, Susi et al. has been reported in the patent literature, e.g., U.S. Pat. No. 3,341,464,"Heat Resistant Aminium Salt Infrared Absorbers" issued Sep. 12, 1967; U.S. Pat. No. 3,400,156, "Triaminotriphenylaminium Salts" issued Sep. 3, 1968; U.S. Pat. No. 3,440,257, "Tris(p-Dialkylaminophenyl) aminium Hexafluoroantimonates and -Arsenates" issued Aug. 22, 1969; U.S. Pat. No. 3,484,467, "Diaryl-(N,N-Diarylaminoaryl)-Aminium Hexafluoroantimonates and Hexafluoro-arsenates" issued Dec. 16, 1969; U.S. Pat. No. 3,575,871, "Tetraaryl Arylaminium Salts and Use as Infrared Absorbers" issued Apr. 20, 1971; and U.S. Pat. No. 3,631,147, "Preparation of Monocation Salts of N,N,N',N'-Tetrakis(p-Dialkyl Aminophenyl)-p-Phenylene-diamines" issued Dec. 28, 1971. Various other patents teach methods of preparation of intermediates and the use of such aminium salts as infrared absorbing components of light filters.

The limited thermal stability of many aminium and related diimmonium salts was immediately recognized. Studies showed that the hexafluoroantimonate ($SbF_6^-$) and, to a somewhat lesser degree, hexafluoroarsenate ($AsF_6^-$) salts of the aminium ions were the most heat resistant. Such work was extended by Cahill, et al., U.S. Pat. No. 7,498,123, with the use of non-coordinating ions such as $(C_6F_5)_4B^-$. Therefore, it is not surprising that the most thermally stable salts of both the aminium and diimmonium chromophores have been widely used as infrared absorbing components in light filters. The diimmonium compositions tend to be less thermally stable than the aminium compositions, and may undergo reduction at elevated temperatures to give the corresponding aminium salt.

One of the most desirable resins or polymers for use in light filters is polycarbonate. Polycarbonate, also frequently referred to by its various trade names, Lexan®, Calibre®, Iupilon®, Makrolon®, etc., can be formulated and molded at high pressure into various shapes in a high temperature process. Polycarbonate's combination of optical and mechanical properties often makes this resin the polymer of choice for ophthalmic and ballistic uses, as well as other applications.

A limiting aspect to the utility of current aminium compositions, particularly in applications such as laser eye protection in which high optical densities are often required for protection against Nd:YAG, Nd:glass, and other laser wavelengths from about 1050 to 1100 nm, is the relatively short peak wavelength of the $(4-R_2N-C_6H_4)_3N^{+\cdot}$ absorption band near 1000 nm.

Another limiting aspect to the utility of current aminium compositions, particularly in applications such as security or authentication in which low visible color in printing, coating, or mass dyeing is required, is the distinct green color of the $(4-R_2N-C_6H_4)_3N^{+\cdot}$ chromophore. The green color of the compositions originates from a combination of an absorption band at blue-violet wavelengths and the absorption due to the tail of the infrared absorption band at red wavelengths.

One path to a solution to the fabrication of light filters with improved light absorption at wavelengths of about 1050 to 1100 nm is to shift the peak wavelength of the aminium dye to longer wavelengths, for example, by increasing the electron donating power of the groups attached to the peripheral nitrogens. However, this approach may be detrimental to the overall performance of the light filter because, by this approach, the blue-violet absorption band of the chromophore may shift to longer wavelengths, possibly decreasing the visible light transmission of the filter.

Accordingly, there is a need for long-wavelength infrared light absorbing compositions that overcome one or more of the aforementioned drawbacks of current compositions. There is also a need to provide light filters using such compositions that are capable of filtering out undesirable, harmful, or dangerous wavelengths of infrared light. There is also a need to provide light filters comprised of plastic resins that have desirable levels of apparent color and infrared absorption. In addition, there is also a need to provide light filters in thin cross-sections or films where highly soluble dyes are required to reach high optical densities, especially in low polarity hosts, for example, hydrocarbons and hydrocarbon polymers, silicones, partially fluorinated liquids or polymers, or other solids, liquids, or gels, or in thin films.

SUMMARY OF THE INVENTION

The present invention is directed to infrared light absorbing aminium or diimmonium compositions that have at least one absorption maximum between about 700 nm and 1500 nm, and filters or sensing materials including these compositions.

In one embodiment, an infrared light absorbing aminium composition is provided that includes an aminium radical cation that has at least one absorption peak in the near infrared wavelength region between about 700 and 1500 nm and has the formula $[4-R^1R^2N-C_6H_3CH_3][4-R^3R^4N-C_6H_3CH_3][4-R^5R^6N-C_6H_3CH_3]N^{+\cdot}$, where $R^1$ through $R^6$ are identical or different, optionally are linked to form rings, and are each an alkyl group, an arylalkyl group, an alkyl ether or hydroxyalkyl group. The composition further includes an anionic borate moiety having the formula $[BX_a Y_b]^-$, in which a and b are integers, and ranges from 0 to 3, b ranges from 1 to 4, and a+b=4. Each X is a halogen atom, which is identical or different or an OH functional group, and each Y, which is identical or different, is a phenyl radical, which is substituted by at least one element or electron-withdrawing substituent or by one or more halogen atoms or an aryl radical containing at least two aromatic ring members, which is optionally substituted.

In another embodiment, an infrared light absorbing diimmonium composition is provided that includes a diimmonium radical dication that has at least one absorption peak in the near infrared wavelength region between about 700 and 1500 nm and has the formula $[4-R^1R^2N-C_6H_3CH_3][4-R^3R^4N-C_6H_3CH_3][4-R^5R^6N-C_6H_3CH_3]N^{+2}$, where $R^1$ through $R^6$ are identical or different, optionally are linked to form rings and are each an alkyl group, an arylalkyl group, an alkyl ether, or hydroxyalkyl group. The composition further includes two anionic borate moieties, with each being identical or different and having the formula $[BX_a Y_b]^-$, in which a and b are integers, and ranges from 0 to 3, b ranges from 1 to 4, and a+b=4. Each X is a halogen atom, which is identical or different or an OH functional group, and each Y, which is identical or different, is a phenyl radical, which is substituted by at least one element or electron-withdrawing substituent or by one or more halogen atoms, or an aryl radical containing at least two aromatic ring members, which is optionally substituted.

In another embodiment, the infrared light absorbing composition further includes a host associated to form an optical filter capable of filtering light.

One object of the present invention is to provide infrared light absorbing compositions that are capable of absorbing light in the range of about 700 to 1500 nm.

Another object of the invention is to provide infrared light absorbing light filters, materials, films, solutions, coatings, or inks.

Another object of the invention is to provide infrared light absorbing compositions that are thermally stable, i.e., that can be processed at about 250° C. or higher, e.g., in polycarbonate molding operations.

Another object of the invention is to provide infrared light absorbing compositions that are soluble in non-polar or low polarity solvents or polymers.

Another object of the invention is to provide a light filter, material, film, solution, coating or ink that is capable of absorbing light in the range of about 700 to 1500 nm.

Another object of the invention is to provide a light filter, material, film, solution, coating or ink that transmits a substantial portion of light at visible wavelengths.

Another object of the invention is to provide infrared light absorbing compositions with greater light transmission than the known aminium compositions.

Another object of the invention is to provide tris(4-aminophenyl)—type infrared light absorbing compositions with longer peak absorption wavelengths than the known aminium compositions of this type.

Another object of the invention is to provide infrared light absorbing compositions with greater solubility in non-polar hosts than those comprised of hexafluoro-antimonate anions.

Another object of the invention is to prepare infrared light absorbing compositions with counterions that lack potentially toxic anions, such as perchlorate, or toxic heavy atoms, such as antimony or arsenic.

Another object of the invention is to prepare filters for electromagnetic radiation, including laser radiation, that include thermally stable infrared light absorbing compositions, alone or in combination with other absorbing dyes, stabilizers or other non- or weakly visible light absorbing additives such as UV-absorbers, light stabilizers, anti-oxidants or free radical trapping agents.

Another object of the invention is to prepare filters for electromagnetic radiation, including laser radiation, that include organic-soluble infrared light absorbing compositions, alone, or in combination with other absorbing dyes, stabilizers, or other non- or weakly visible light absorbing additives such as UV-absorbers, light stabilizers, anti-oxidants, or free radical trapping agents.

Another object of the invention is to prepare filters for electromagnetic radiation in forms such as plaques, spectacles, visors, or contact lenses.

Another object of the invention is to prepare infrared light absorbing compositions that are chemically, thermally and photochemically compatible with optical filter, material, film, solution, coating or ink manufacturing processes, and with processes for depositions of subsequent coatings, if any. Such processes may include molding, casting, imbibing, thermal curing or radiation or UV curing, among others.

Another object of the invention is to improve the manufacturing-related metrics of reproducibility and consistency of the transmittance and optical density of filters, materials, films, solutions, coatings or inks including infrared light absorbing compositions.

Another object of the invention is to reduce the cost of manufacturing infrared absorbing filters by minimizing the additional amount of the infrared light absorbing composition that is often required to make up for decomposition of less thermally stable infrared absorbing dyes.

Another object of the invention is to increase the luminous transmission of infrared absorbing filters, materials, films, solutions, coatings or inks by reducing the decomposition of thermally sensitive infrared absorbing compositions.

Another object of the invention is to provide filters, materials, films, solutions, coatings or inksincluding infrared absorbing compositions from plastic resins that are compatible with processes used to deposit coatings on polymeric substrates.

Another object of the invention is to provide filters from plastic resins that are optionally impact resistant. Such plastic resins and filters are optionally polycarbonate. Such plastic resins and filters are optionally of ophthalmic quality. Such plastic resins and filters optionally offer impact or ballistic protection. The filters, films, or substrates may be in any shape useful to their end-purpose, e.g., a curved lens or visor for eye protection or a flat sheet for a vision system.

Another object of the invention is to prepare notch, long pass, short pass, and band pass filters for optical filter applications by substituting an infrared absorbing dye from the prior art with at least one infrared absorbing composition into or onto a substrate that is optionally compatible with absorptive and/or diffractive and/or reflective coatings.

The present invention can achieve one or more of these objectives by providing infrared light absorbing compositions, including, for example, tris(aminophenyl aminium)-type dyes having ortho-methyl substituted phenyl groups, which can be incorporated into optical filters, materials, films, solutions, coatings or inks for filtering or emitting light, which address weaknesses and drawbacks of previously proposed materials. Particularly, certain infrared light absorbing compositions have greater luminous transmission for a given optical density in the infrared. Such compositions can be useful in a variety of applications, including those where high transmittance across much of the visible light spectrum and low transmittance at certain wavelengths in the infrared are required. For example, the infrared light absorbing compositions may be used in information displays, such as holographic displays, filters for laser radiation, illumination sources, photographic processes, and light emitting diodes including organic light emitting diodes, security inks and resins, eye protection, and sensors.

By virtue of the foregoing, there are described herein infrared light absorbing aminium or diimmonium compositions that are chemically, thermally, and/or photochemically compatible with known manufacturing processes, and with known processes such as for deposition as coatings or inks.

The features and objectives of the present invention will become more readily apparent from the following Detailed Description taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention.

DETAILED DESCRIPTION

The present invention is directed to infrared light absorbing aminium and diimmonium compositions that have at least one absorption maximum between about 700 nm and 1500 nm, and filters or sensing materials including these compositions.

In one embodiment, there is provided an infrared light aminium absorbing composition including an anionic borate moiety and an aminium radical cation, which has at least one absorption peak in the near infrared wavelength region between about 700 and 1500 nm. The aminium radical cationic can include the formula $[4-R^1R^2N-C_6H_3CH_3][4-R^3R^4N-C_6H_3CH_3][4-R^5\ R^6N-C_6H_3CH_3]N^{+\cdot}$, and the anionic borate moiety can have the formula $[BX_aY_b]^-$.

With respect to the aminium radical cation, $R^1$ through $R^6$ can be identical or different, optionally are linked to form rings and are each an alkyl group, an arylalkyl group, an alkyl ether group or hydroxy alkyl group, optionally linked or chemically bound to an oligomer or polymer. The peak absorption wavelength can be tuned by changing the R groups. And with respect to the anionic borate moiety, a and b can be integers and a can range from 0 to 3 and b can range from 1 to 4, and a+b=4. Each X can be a halogen atom, which may be identical or different or an OH functional group, and each Y, which may be identical or different, can be a phenyl radical, which is substituted by at least one element or electron-withdrawing substituent, such as a perfluoroalkyl group, or by one or more halogen atoms or an aryl radical containing at least two aromatic ring members, which is optionally substituted.

Figure 1:
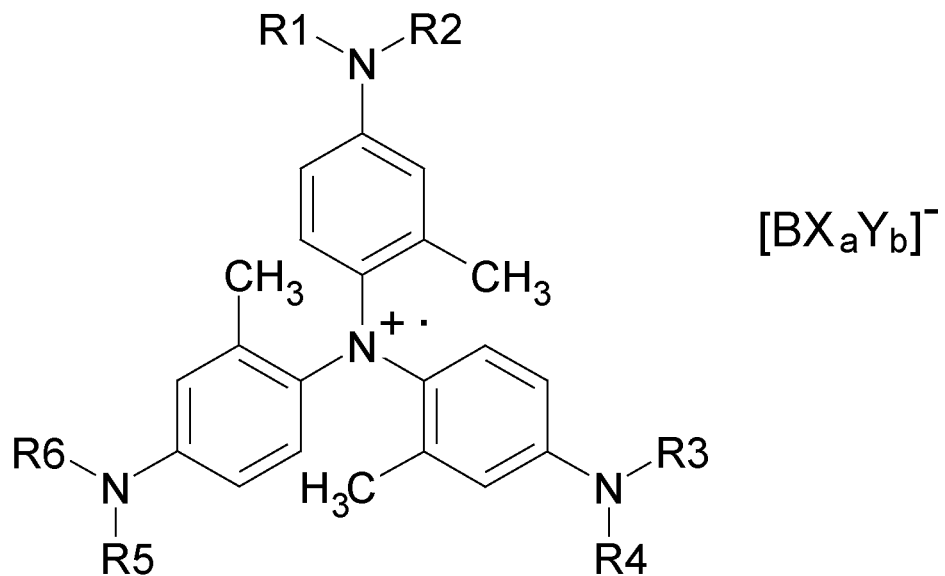
FIG. 1 is an infrared light absorbing composition in accordance with an embodiment of the invention including an aminium radical cation with one methyl group on each arene and ortho- to the central nitrogen.

As shown in FIG. 1, in one example, the infrared light absorbing aminium composition includes a tri-methyl aminium ion wherein each of the $-CH_3$ groups in the formula is ortho- to the central nitrogen. This infrared light absorbing aminium composition shows a distinctive infrared absorption band near 1062 nm in acetone and near 1075 nm in polycarbonate resin when $R^1-R^6$=n-butyl. In another example, the alkyl ether group can include oligo ethylene glycol ethers. In another example, the hydroxy alkyl group can include hydroxy ethyl.

In another example, $R^1$ through $R^6$ can be hydrocarbons having the formula $(4-G_2N-C_6H_3CH_3)_3N^{+\cdot}$, wherein each G is selected from methyl, ethyl, propyl, isopropyl, butyl, isobutyl, pentyl, isoamyl, hexyl, octyl, ethylhexyl, decyl, dodecyl or benzyl. In another example, $R^1$ through $R^6$ is n-butyl.

In another embodiment, there is provided an infrared light absorbing diimmonium composition including two anionic borate moieties, which may be the same or different, and a diimonium dication, which has at least one absorption peak in the near infrared wavelength region between about 700 and 1500 nm. The diimmonium radical dication can have the formula $[(4-R^1R^2NC_6H_3CH_3)(4-R^3R^4NC_6H_3CH_3)N=C_6H_3CH_3=NR^5R^6]^{2+}$, and the anionic borate moiety can have the formula $[BX_aY_b]^-$.

with respect to the diimmonium radical dication, $R^1$ through $R^6$ can be identical or different, optionally are linked to form rings and are each an alkyl group, an arylalkyl group, an alkyl ether group or hydroxy alkyl group, optionally linked or chemically bound to an oligomer or polymer. The peak absorption wavelength can be tuned by changing the R groups. And with respect to the anionic borate moiety, a and b can be integers and a can range from 0 to 3 and b can range from 1 to 4, and a+b=4. Each X can be a halogen atom, which may be identical or different or an OH functional group, and each Y, which may be identical or different, can be a phenyl radical, which is substituted by at least one element or electron-withdrawing substituent, such as a perfluoroalkyl group or by one or more halogen atoms, or an aryl radical containing at least two aromatic ring members, which is optionally substituted.

Figure 2:
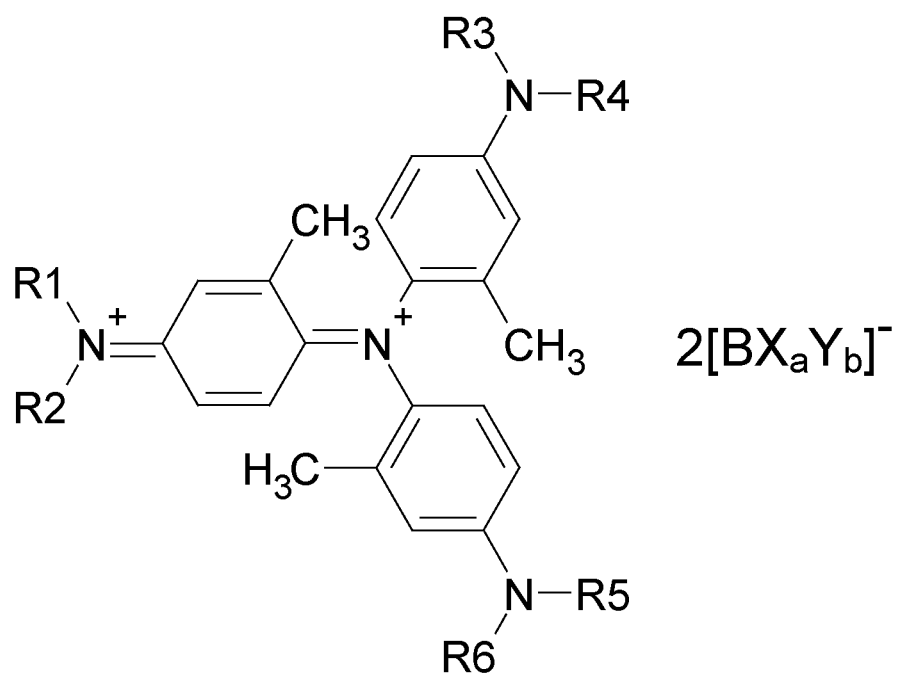
FIG. 2 is an infrared light absorbing composition in accordance with an embodiment of the invention including a diimmonium dication with one methyl group on each arene and ortho- to the central nitrogen.

As shown in FIG. 2, in one example, the infrared light absorbing diimmonium composition includes a tri-methyl diimmonium ion wherein each of the —$CH_3$ groups in the formula is ortho- to the central nitrogen. In another example, the alkyl ether group can include oligo ethylene glycol ethers. In another example, the hydroxy alkyl group can include hydroxy ethyl.

In another example, $R^1$ through $R^6$ can be hydrocarbons having the formula $(4-G_2N—C_6H_3CH_3)_3N^{+2}$, wherein each G is selected from methyl, ethyl, propyl, isopropyl, butyl, isobutyl, pentyl, isoamyl, hexyl, octyl, ethylhexyl, decyl, dodecyl or benzyl. In another example, $R^1$ through $R^6$ is n-butyl.

In one example, the anionic borate moiety in the infrared light absorbing aminium or diimmonium composition can include $[3,5-(CF_3)_2C_6H_3]_4B^-$, $[(CF_3)C_6H_4]_4B^-$, $[(C_6F_5)_3BF]^-$, $[(C_6F_5)_2BF_2]^-$, $[(C_6F_5)_2BF_3]^-$, $(C_6F_5)_4B^-$, or $[(CF_3)C_6H_2F_2]_4B^-$. In another example, the borate anion is $(C_6F_5)_4B^-$.

In another embodiment, the infrared light absorbing composition further includes a host associated therewith to form an optical filter capable of filtering light.

With respect to the ortho- positioned methyl groups, by incorporating the methyl groups onto the phenyl rings in positions ortho- to the central nitrogen in the infrared light absorbing composition, the infrared band shifts to longer wavelengths and the blue violet band simultaneously and unexpectedly shifts to shorter wavelengths relative to those compositions without the methyl groups. The effect of these dual shifts of both the visible and infrared bands serves to reduce the apparent color and increase the blue and red light transmission of a light filter designed for a particular optical density at wavelengths near 1000-1200 nm in the infrared, regardless of the specific application of the filter.

Also, the infrared light absorbing compositions that incorporate one or more methyl groups onto the phenyl rings in positions ortho- to the central nitrogen, unexpectedly show, in some cases, melting points near or below room temperature and generally have very high solubility in organic solvents. The high solubility of the dyes in organic solvents facilitates the fabrication of thin film filters comprised of such dyes.

The light absorbing aminium and diimmonium compositions generally absorb infrared light over a range of wavelengths and are useful for various light-filtering applications. The compositions may further include more than one light-absorbing compound. The additional light-absorbing compound(s) may also be aminium salts, diimmonium salts, polymethines, porphyrins, azaporphyrins, phthalocyanines, squarylium compounds, dithiolenes, etc., as such compounds are well known in the art. The compositions may also include additional reflective, refractive and/or diffractive elements capable of filtering and or transmitting optical radiation from the ultraviolet wavelengths through the infrared wavelengths. Furthermore, other dyes, light stabilizers, UV-absorbers, anti-oxidants, quenchers and the like may be included in the composition.

When combined with a host, the infrared light-absorbing compositions, and other optional compounds, can generally form a light-filtering device. The host is generally either a liquid, a gel or a solid. For example, the host may be a matrix material or a film. In one embodiment, the host is a material selected from the group consisting of polycarbonate, polystyrene, polyvinyl chloride, polyacrylate, polyurethane, polymethylmethacrylate, silicone, silicon-based polymers, glass, sol-gel, hydrogel, polycrystalline materials, plastic, cellulose derivatives and combinations thereof. The light absorbing aminium or diimmonium compositions may be, without limitation, a coating on or an integral part of the host material. For example, optical filters may be fabricated by one of several conventional methods, such as injection molding, for incorporating the compositions into or onto various hosts.

The resulting filter may include other additives or dyes to provide, for example, UV stabilization or a tailored spectral curve. The filter includes a host in combination with at least one of the light absorbing aminium or diimmonium compositions that has at least one absorption maximum in the near infrared spectral region between about 700 and 1500 nm. Again, such light absorbing aminium and diimmonium compositions can be useful in filters, either alone or in combination with other absorptive, reflective, refractive, or diffractive elements for optical radiation from the ultraviolet through the infrared.

Figure 3:
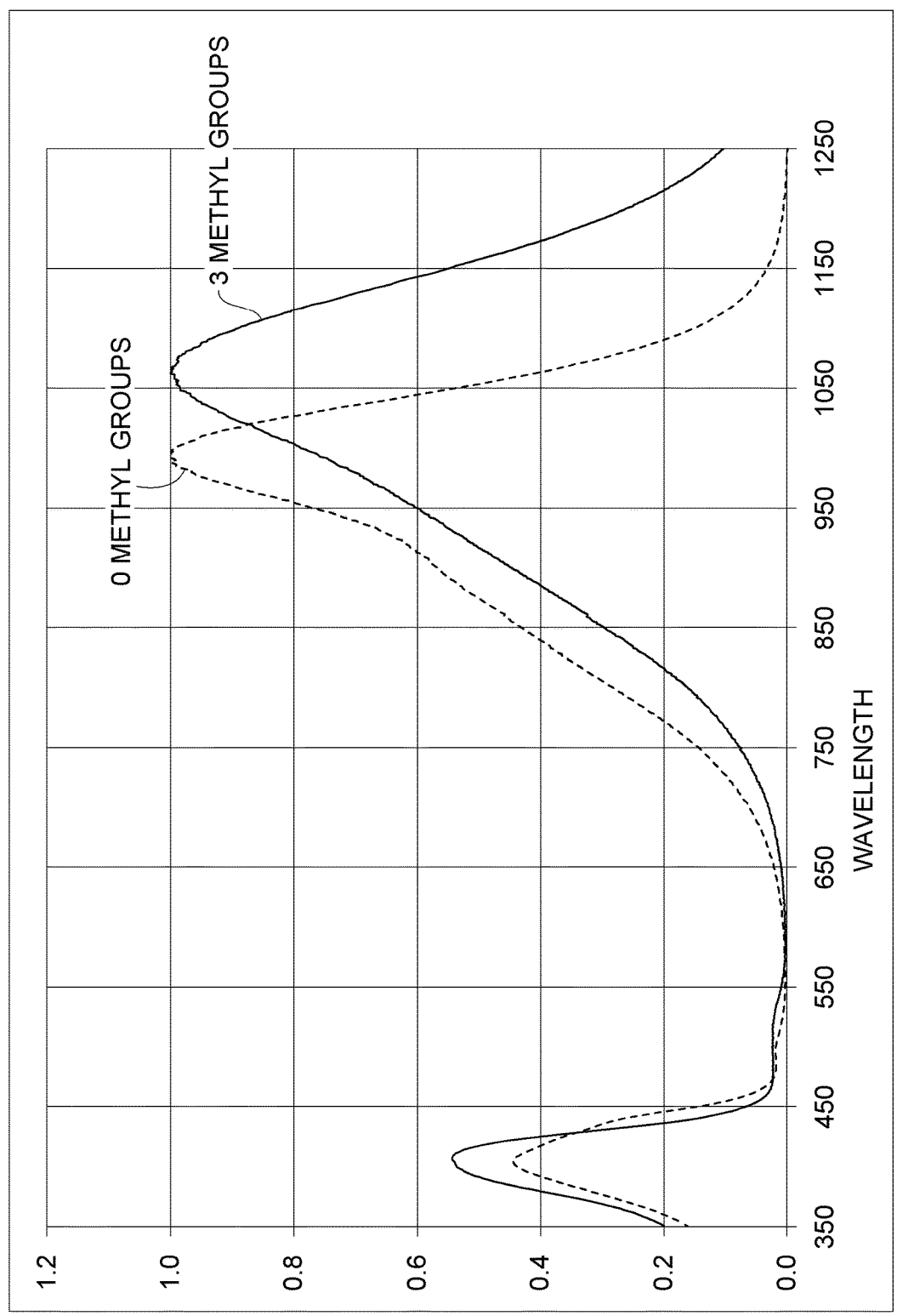
FIG. 3 is a graph that demonstrates the shift to longer wavelengths in two infrared light absorbing compositions including an aminium radical cation, with 0 and 3 methyl groups.

With respect to preparation of the light absorbing aminium and diimmonium compositions, by way of example, the aminium cation of the type shown in FIG. 1 can be prepared from $(4-Bu_2NC_6H_3CH_3)_3N$ and about one equivalent of a silver salt, for example, $Ag^+(C_6F_5)_4B^-$, in a suitable solvent, such as methylene chloride, under conditions known to be useful for the synthesis of aminium cations. The resulting product may be isolated and purified by techniques such as extraction, crystallization, and chromatographic separation. More specifically, the amine $(4-Bu_2NC_6H_3CH_3)_3N$ can be prepared in multiple steps. First, the triaryl framework can be prepared from 2-fluoro-5-nitrotoluene and 2-methyl-4-nitroaniline in two steps in DMF solvent according to the known methods described by Gorvin, J. C. S. Perkin Transactions I, 1988, pp 1331-1335, which is incorporated herein by reference in its entirety. Then, reduction of the resulting $(4-O_2NC_6H_3CH_3)_3N$ intermediate can be carried out by use of hydrazine hydrate in DMF over a Pd/C catalyst and the resulting $(4-H_2NC_6H_3CH_3)_3N$ can be alkylated by standard techniques with an alkyl halide, by example, 1-bromobutane in DMF with $K_2CO_3$ or 1-iodobutane in ethanol with $Na_2CO_3$. The aminium cation with a borate counterion $(4-Bu_2NC_6H_3CH_3)_3N^+\cdot(C_6F_5)_4B^-$ was prepared by the addition of a solution of about 1 equivalent of $Ag^+(C_6F_5)_4B^-$ in methylene chloride to a solution of $(4-Bu_2NC_6H_3CH_3)_3N$ in methylene chloride from about −20 to about 0° C. After warming the solution to room temperature overnight, the precipitate was filtered off and the filtrate was purified by chromatography on silica gel with methylene chloride eluent. The peak wavelength of the dye in acetone was observed at about 1062 nm and the edge of the violet band was observed at about 436 nm. Notably, the peak wavelength of the aminium composition with three methyl groups is shifted about 70 nm to longer wavelengths from the dye without the added methyl groups. See Tables I and II below, which are discussed next. See also FIG. 3, which shows absorption spectra of the prepared aminium composition for 0 and 3 methyl groups (in the ortho position to the central nitrogen), normalized at the infrared peak, $R^1$-$R^6$=butyl.

Tables I and II below list the wavelength of infrared light absorbing aminium compositions with 0 and 3 methyl groups (in the ortho position to the central nitrogen). The observation that the peak wavelengths of aminium compositions increase with changes in alkyl groups on the nitrogen from, for example, ethyl to butyl is well known. However, less well understood is the effect of one or more methyl groups on the phenyl rings and ortho- to the central nitrogen. The reason for the effect of the methyl groups on peak wavelength may or may not be associated with an increase in propeller angle of the phenyl groups at the central nitrogen.

Overall, the improvement in blue and red light transmission as well as the solubility of the infrared absorbing tri(methylphenyl) compositions was unexpected.

TABLE I

Aminium Chromophore Spectral Properties, Acetone

| Chromophore | Peak Wavelength (Acetone) about +/−10 nm | Visible Cut-off wavelength (20% of IR absorption) | Percentage of peak absorption at 1064 nm | Full Width Half Maximum (FWHM, nm) |
|---|---|---|---|---|
| $[(Bu_2N)C_6H_4]_3N^{+\cdot}$ | 993 nm | 445 nm | 39% | 179 nm |
| $[(Bu_2N)C_6H_4CH_3]_3N^{+\cdot}$ | 1062 nm | 436 nm | 99% | 240 nm |

TABLE II

Aminium Chromophore Spectral Properties, Polycarbonate

| Chromophore | Peak Wavelength (Polycarbonate) about +/−10 nm | Visible Cut-off wavelength (20% of 1064 nm absorption) | Percentage of peak absorption at 1064 nm | Full Width Half Maximum (FWHM, nm) |
|---|---|---|---|---|
| $[(Bu_2N)C_6H_4]_3N^{+\cdot}$ | 1005 nm | 456 nm | 55% | 182 nm |
| $[(Bu_2N)C_6H_3CH_3]_3N^{+\cdot}$ | 1073 nm | 440 nm | 99% | 250 nm |

Figure 4:
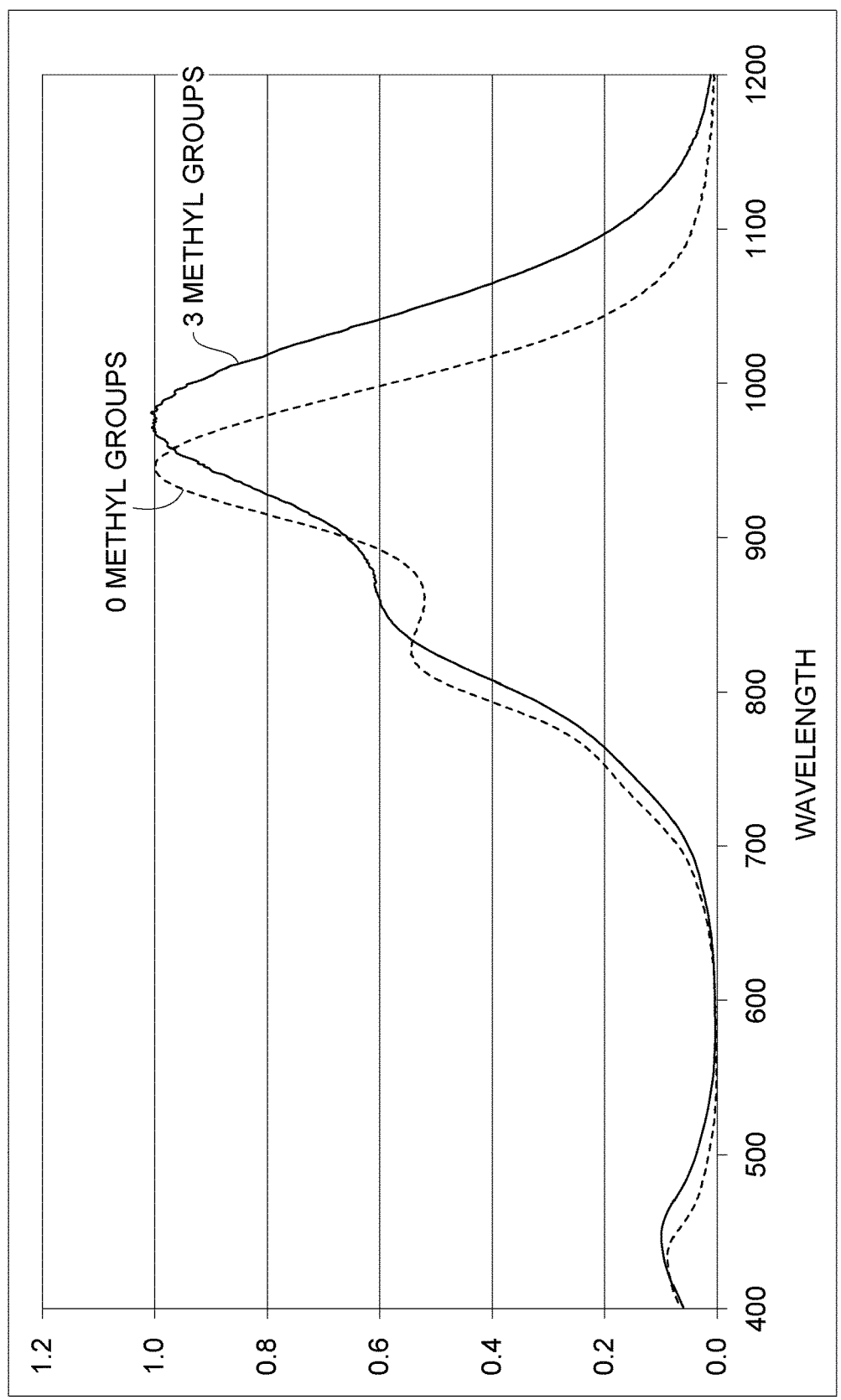
FIG. 4 is a graph that demonstrates the shift to longer wavelengths in two infrared light absorbing compositions including a diimmonium dication, with 0 and 3 methyl groups.

Further, by way of example, the diimmonium cation of the type shown in FIG. 2 can be prepared from $(4\text{-}Bu_2NC_6H_3CH_3)_3N$ and a minimum of about two equivalents of a silver salt, for example, $Ag^+(C_6F_5)_4B^-$, in a suitable solvent, such as methylene chloride, under conditions known to be useful for the synthesis of diimmonium cations. The resulting product may be isolated and purified by techniques such as extraction, crystallization, and chromatographic separation. More specifically, the diimmonium dication shown in FIG. 2 with a borate counterion $(4\text{-}Bu_2NC_6H_3CH_3)_3N^{+2}$ $[(C_6F_5)_4B^-]_2$ was prepared by the addition of a solution of about 2 equivalents of $Ag^+(C_6F_5)_4B^-$ in methylene chloride to a solution of $(4\text{-}Bu_2NC_6H_3CH_3)_3N$ in methylene chloride from about −20 to about 0° C. Upon warming to room temperature, the precipitate was filtered off and the filtrate was purified by chromatography on silica gel with methylene chloride eluent. The peak wavelength of the dye in methylene chloride was observed at about 975 nm. See also FIG. 4, which shows the absorption spectra of the prepared diimmonium composition for 0 and 3 methyl groups (in the ortho- position to the central nitrogen), normalized at the infrared peak, showing increasing peak wavelength in nanometers with increasing number of methyl groups.

While the present invention has been illustrated by the description of embodiments thereof, and while the embodiments have been described in considerable detail, it is not intended to restrict or in any way limit the scope of the appended claims to such detail. Additional advantages and modifications will be readily apparent to those skilled in the art. The invention in its broader aspects is therefore not limited to the specific details, representative apparatus and method, and illustrated examples described. Accordingly, departures may be made from such details without departing from the scope of the Applicant's general inventive concept.

What is claimed is:

1. An infrared light absorbing aminium composition comprising:
   an aminium radical cation that has at least one absorption peak in the near infrared wavelength region between about 700 and 1500 nm and having the formula:

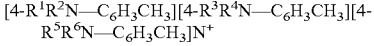
   $[4\text{-}R^1R^2N\text{—}C_6H_3CH_3][4\text{-}R^3R^4N\text{—}C_6H_3CH_3][4\text{-}R^5R^6N\text{—}C_6H_3CH_3]N^+$ where $R^1$ through $R^6$ are identical or different, optionally are linked to form rings, and are each an alkyl group, an arylalkyl group, an alkyl ether, or hydroxyalkyl group, and
   an anionic borate moiety having the formula:

   $[BX_aY_b]^-$ in which a and b are integers, and a ranges from 0 to 3, b ranges from 1 to 4, and a+b=4; each X is a halogen atom, which is identical or different or an OH functional group, and each Y, which is identical or different, is a phenyl radical, which is substituted by at least one element or electron-withdrawing substituent or by one or more halogen atoms, or an aryl radical containing at least two aromatic ring members, which is optionally substituted.

2. The composition of claim 1, wherein $R^1$ through $R^6$ are hydrocarbons, having the formula $(4\text{-}G_2N\text{—}C_6H_3CH_3)_3N^{+\cdot}$, wherein each G is selected from methyl, ethyl, propyl, isopropyl, butyl, isobutyl, pentyl, isoamyl, hexyl, oxtyl, ethylhexyl, decyl, dodecyl, or benzyl.

3. The composition of claim 1, wherein the anionic borate moiety is $(C_6F_5)_4B^-$.

4. The composition of claim 1, wherein the anionic borate moiety is selected from $[3,5\text{-}bis(CF_3)_2C_6H_3]_4B^-$, $[(CF_3)C_6H_4]_4B^-$, $[(C_6F_5)_3BF]^-$, $[(C_6F_5)_2BF_2]^-$ or $[(C_6F_5)BF3]^-$.

5. The composition of claim 1, wherein $R^1$ through $R^6$ is n-butyl.

6. The composition of claim 1, wherein the methyl group on each arene in the aminium radical cation formula is ortho- to the central nitrogen.

7. A filter or filter element including the composition of claim 1, alone or in combination with one or more dyes, absorbers and/or additives.

8. A filter or filter element including the composition of claim 1, which is chemically bound to an oligomer or polymer.

9. The filter or filter element of claim 7 further including a liquid, gel, or solid in which the composition is dispersed.

10. The filter or filter element of claim 7 defining one of an optical wavelength filter, display filter, illumination source filter or laser radiation filter.

11. A contact lens including the composition of claim 1.

12. An infrared light absorbing diimonium composition comprising:

a diimonium radical dication that has at least one absorption peak in the near infrared wavelength region between about 700 and 1500 nm and having the formula:

[4-$R^1R^2$N—$C_6H_3CH_3$][4-$R^3R^4$N—$C_6H_3CH_3$][4-$R^5R^6$N—$C_6H_3CH_3$]$N^{+2}$ where $R^1$ through $R^6$ are identical or different, optionally are linked to form rings, and are each an alkyl group, an arylalkyl group, an alkyl ether or hydroxyalkyl group, and two anionic borate moieties, with each being identical or different and having the formula:

[$BX_aY_b$]$^-$ in which a and b are integers, and a ranges from 0 to 3, b ranges from 1 to 4, and a+b=4; each X is a halogen atom, which is identical or different or an OH functional group, and each Y, which is identical or different, is a phenyl radical, which is substituted by at least one element or electron-withdrawing substituent or by one or more halogen atoms, or an aryl radical containing at least two aromatic ring members, which is optionally substituted.

13. The composition of claim 12, wherein $R^1$ through $R^6$ are hydrocarbons, having the formula (4-$G_2$N—$C_6H_3CH_3$)$_3$$N^{+2}$, wherein each G is selected from methyl, ethyl, propyl, isopropyl, butyl, isobutyl, pentyl, isoamyl, hexyl, oxtyl, ethylhexyl, decyl, dodecyl, or benzyl.

14. The composition of claim 12, wherein at least one anionic borate moieties is ($C_6F_5$)$_4$$B^-$.

15. The composition of claim 12, at least one anionic borate moiety is selected from [3,5-bis($CF_3$)$_2$$C_6H_3$]$_4$$B^-$, [($CF_3$)$C_6H_4$]$_4$$B^-$, [($C_6F_5$)$_3$BF]$^-$, [($C_6F_5$)$_2$$BF_2$]$^-$ or [($C_6F_5$)$BF3$]$^-$.

16. The composition of claim 12, wherein $R^1$ through $R^6$ is n-butyl.

17. The composition of claim 12, wherein the methyl group on each arene in the diimonium radical dication formula is ortho- to the central nitrogen.

18. A filter or filter element including the composition of claim 12, alone or in combination with one or more dyes, absorbers or additives.

19. A filter or filter element including the composition of claim 12, which is chemically bound to an oligomer or polymer.

20. The filter or filter element of claim 18 further including a liquid, gel, or solid in which the composition is dispersed.

21. The filter or filter element of claim 18 defining one of an optical wavelength filter, display filter, illumination source filter or laser radiation filter.

22. A contact lens including the composition of claim 12.

* * * * *